US00PP33589P2

(12) United States Plant Patent
Moon

(10) Patent No.: US PP33,589 P2
(45) Date of Patent: Nov. 2, 2021

(54) ***THUJA* PLANT NAMED 'TPMTF'**

(50) Latin Name: ***Thuja plicata* x *standishii***
Varietal Denomination: TPMTF

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 17/235,477

(22) Filed: Apr. 20, 2021

(51) Int. Cl.
*A01H 7/00* (2006.01)
*A01H 6/00* (2018.01)

(52) U.S. Cl.
USPC ..... Plt./213
CPC ..... *A01H 6/00* (2018.05)

(58) Field of Classification Search
USPC ..... Plt./213
CPC ..... A01H 7/00
See application file for complete search history.

*Primary Examiner* — Kent L Bell
(74) *Attorney, Agent, or Firm* — Cassandra Bright

(57) ABSTRACT

A new and distinct *Thuja* cultivar named 'TPMTF' is disclosed, characterized by dark green foliage on dense plants with upswept branches. Plants have been observed to tolerate high temperatures in the Southern United States. The new cultivar is a *Thuja,* suitable for ornamental garden purposes.

3 Drawing Sheets

Latin name of the genus and species: *Thuja plicata* x *standishii.*

Variety denomination: 'TPMTF'.

BACKGROUND OF THE INVENTION

The new cultivar, hereinafter referred to as 'TPMTF', was discovered by the inventor, Dwayne Moon, in a commercial nursery in Washington, Ga. This new variety was discovered growing as an individual plant among a group of branch sport *Thuja plicata* x *standishii* 'Green Giant' (unpatented). The inventor identified this interesting new variety during the Summer of 2013 in his production field.

After identifying the new variety as a potentially interesting selection during 2013, the inventor first organized propagation of 'TPMTF' by softwood cuttings at the same commercial nursery late 2013. The inventor continued controlled testing and propagation, assessing stability of the unique characteristics of this variety. At least five generations have been reproduced and have shown that the unique features of this cultivar are stable and reproduced true to type.

SUMMARY OF THE INVENTION

The cultivar 'TPMTF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TPMTF' These characteristics in combination distinguish 'TPMTF' as a new and distinct *Thuja* cultivar:

1. Dark green foliage.
2. Narrow width, about 50% of typical *Thuja plicata* x *standishii.*
3. No bell shape on bottom.
4. Close bud set.
4. Dense canopy.

5. Upswept branch structure.
6. Observed heat tolerance in the Southern United States.

COMPARISON TO PARENT VARIETY

'TPMTF' is similar in most horticultural characteristics to the parent variety *Thuja plicata* x *standishii*. 'Green Giant'. Plants of the new cultivar 'TPMTF' however, differ in the following:

1. New cultivar grows more slowly than the parent variety.
2. New cultivar has denser foliage and darker green foliage.
3. The new variety produces branches at a more upright angle than the parent.
4. The new variety is overall smaller in both height and width than the parent.
5. The top of the plant of the new variety branches more densely than plants of the parent.

COMMERCIAL COMPARISON

*Thuja* 'TPMTF' can be compared to the commercial variety *Thuja plicata* 'Fastigiata' (unpatented). Plants are similar in most horticultural characteristics, however, plants of the new variety differ in the following:

1. 'TPMTF' grows overall smaller in both height and width than this comparator.
2. 'TPMTF' is a fuller plant on the top.
3. The new variety does not grow as rapidly as this comparator.

*Thuja* 'TPMTF' can be compared to the commercial variety *Thuja plicata* 'Green Splendor' (aka 'Hoyt') (unpatented). Plants are similar in most horticultural characteristics, however, plants of the new variety differ in the following:

1. 'TPMTF' grows overall smaller in both height and width than this comparator.
2. 'TPMTF' is a fuller plant on the top.

3. The new variety does not grow as rapidly as this comparator.

*Thuja* 'TPMTF' can be compared to the commercial variety *Thuja plicata* 'Stribling' (unpatented). Plants are similar in most horticultural characteristics, however, plants of the new variety differ in the following:

1. 'TPMTF' grows into a narrow obovate shape, this comparator is highly columnar.

BRIEF DESCRIPTION OF THE PHOTOGRAPHS

The accompanying photograph in FIG. 1 illustrates in full color typical plants of 'TPMTF' grown outdoors in Washington, Ga. The plants are approximately 2 to 3 years old, shown growing in the ground.

Figure 1:
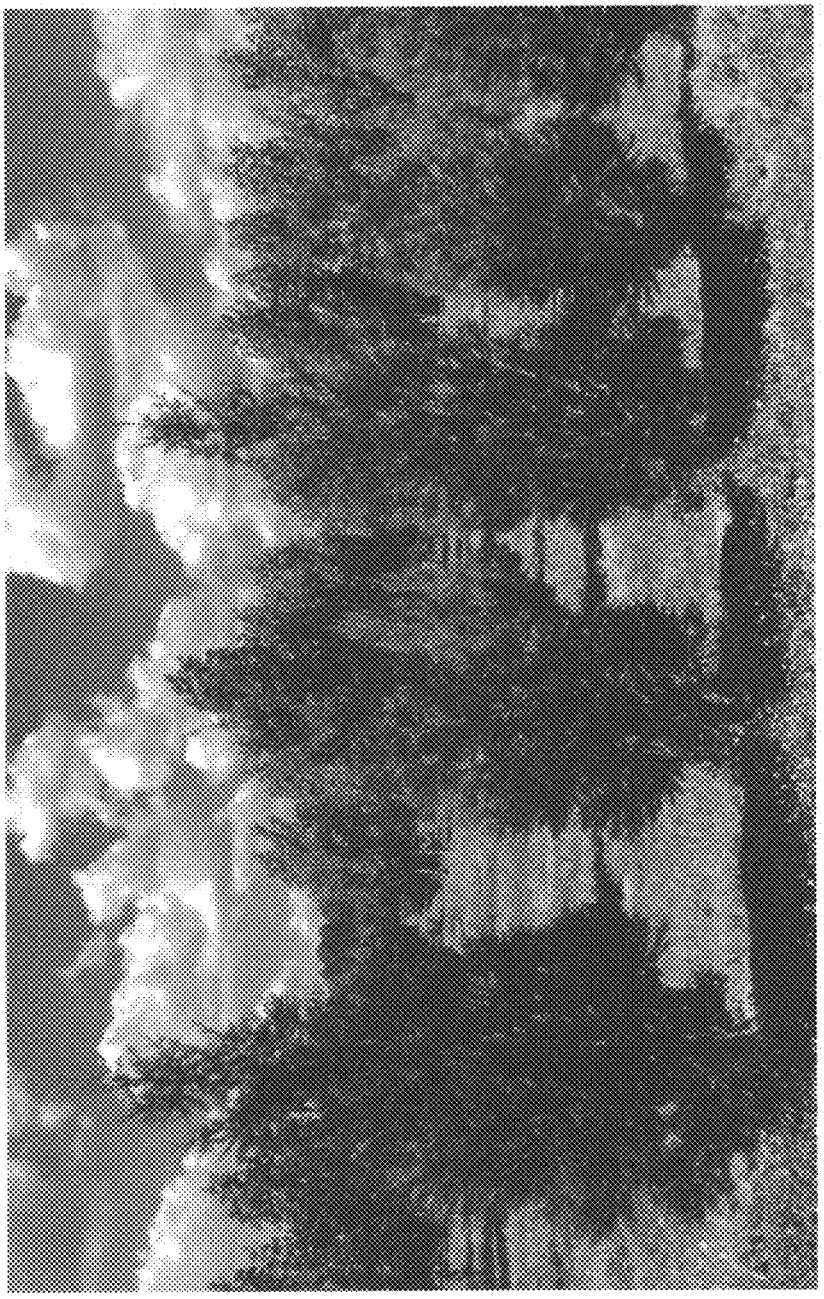
Figure 2:
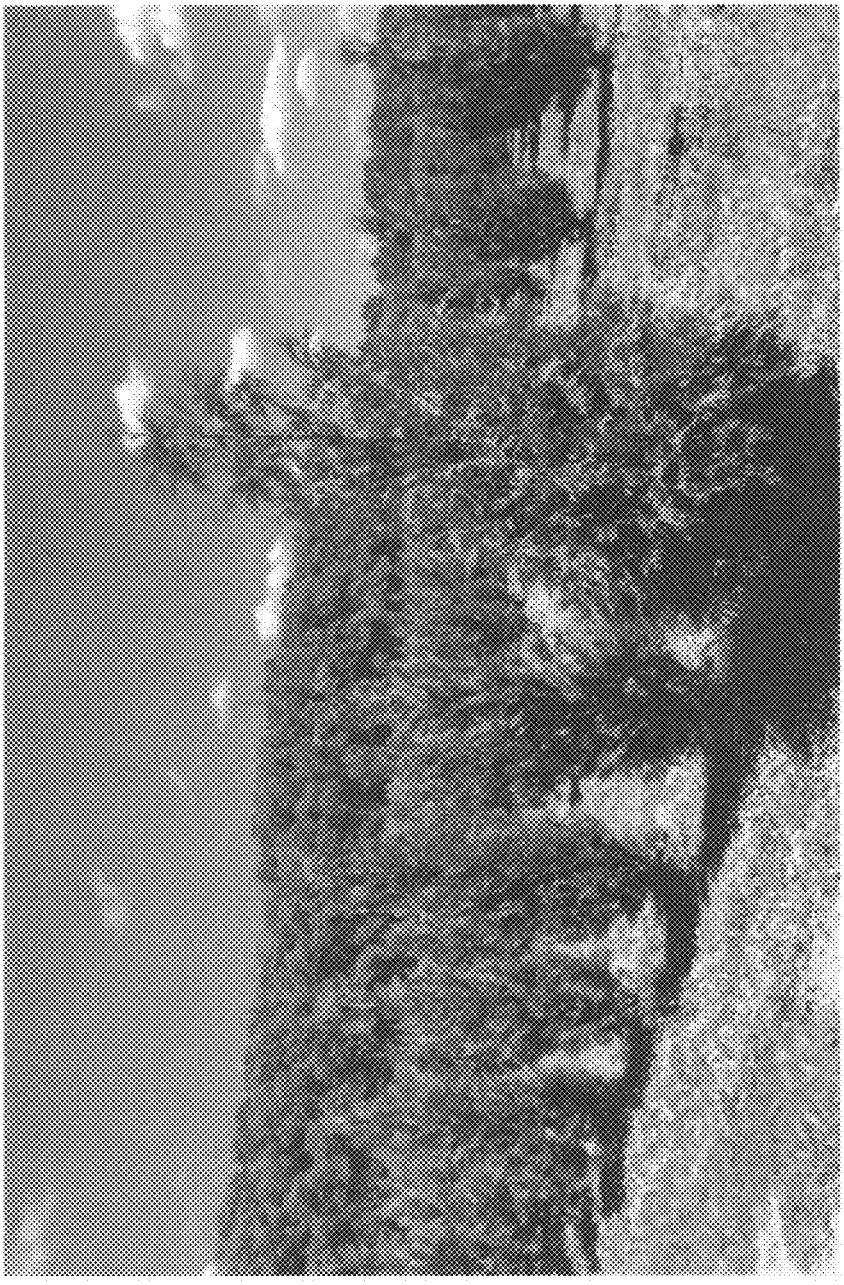
FIG. 2 illustrates a row of plants of the new variety, with a plant of the parent variety growing at the front of the row. Plants are the same age, with the parent variety significantly larger at the same age (2 to 3 years).
Figure 3:
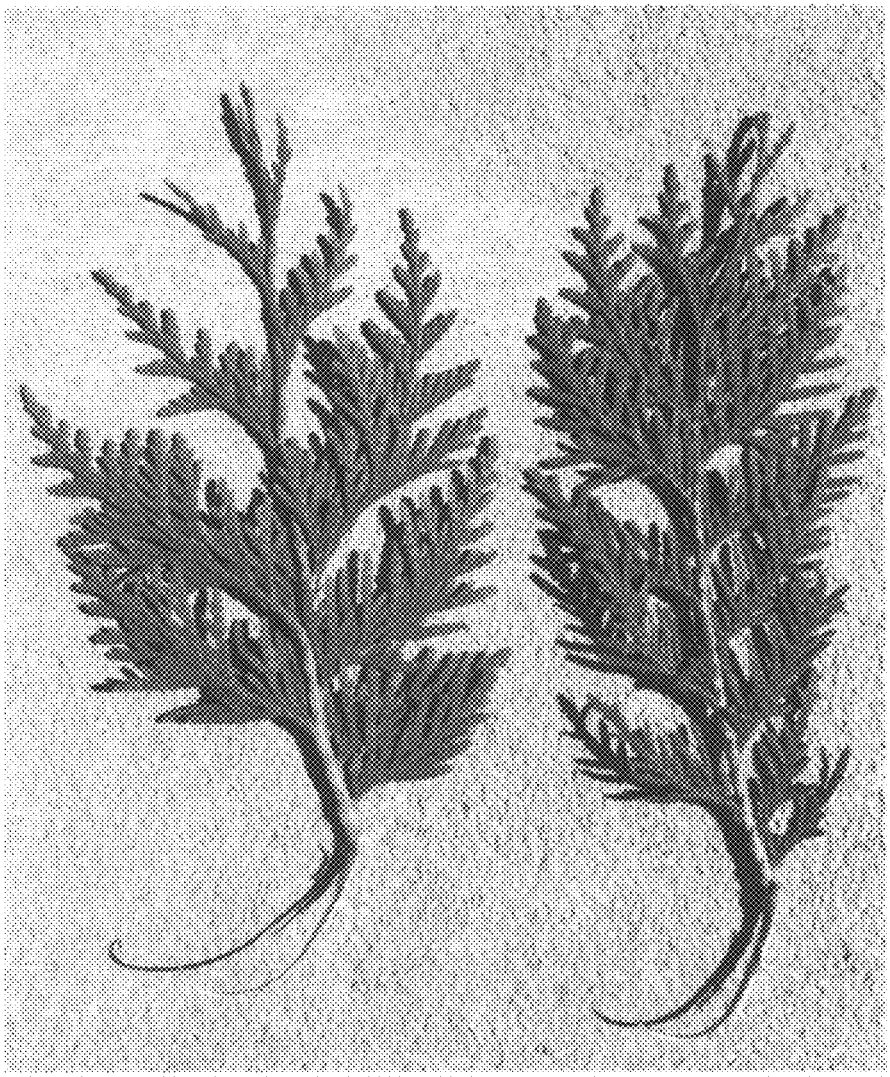
FIG. 3 shows a close up of typical foliage of the new variety (bottom of figure), and foliage of the parent variety (top of figure).

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'TPMTF' plants grown outdoors in Loganville, Ga. Plants are approximately 2-3 years old, in a 3 gallon nursery container. Measurements and numerical values represent averages of typical plant types.

Botanical classification: *Thuja plicata* x *standishii* 'TPMTF'.

PROPAGATION

Time to rooting: 60 to 90 days at approximately 40-50° F.

Root description: Thick to fine, fibrous and fleshy, moderate branching. Colored white to tan, not accurately measured with the RHS chart.

PLANT

Growth habit: Upright, with upswept branches, overall narrow obovate.

Height: 150 cm.

Plant spread: 60 cm.

Typical growth rate: Moderate.

Pinching required: Some pinching encourages better branching.

Branching habit: Occurring from center, upswept, acute.

Length of lateral branches: 30 cm.

Average number of lateral branches: 25-50.

Diameter of lateral branches: 8 mm.

Lateral branch color: Brown N200B.

Lateral branch strength: Strong.

Internode length: 1 cm, on average.

FOLIAGE

Leaf:

*Arrangement.*—Alternate, scales.

*Shape.*—Scale-like.

*Average length.*—5 mm.

*Average width.*—1 mm.

*Apex.*—Acuminate.

*Base.*—Truncate.

*Margin.*—Entire.

*Texture of top surface.*—Glabrous.

*Texture of bottom surface.*—Glabrous.

*Color.*—Young foliage upper side: Near RHS Green 143C flushed Yellow-Green N144B. Young foliage under side: Near RHS Green 143C flushed Yellow-Green N144B. Mature foliage upper side: Near RHS Green 139A. Mature foliage under side: Near RHS Green 137A.

*Venation.*—Indistinguishable from leaf blade.

*Fragrance.*—Cedarlike.

FLOWER

Flowering not observed.

OTHER CHARACTERISTICS

Disease and pest resistance: Deer resistant. No other resistance nor susceptibility observed.

Drought tolerance: No tolerance for drought observed. *Thuja plicata* can be moderately drought tolerance once established.

Temperature tolerance: USDA Zones 5-9.

What is claimed is:

1. A new and distinct cultivar of *Thuja* plant named 'TPMTF' as herein illustrated and described.

* * * * *